United States Patent
Metzger et al.

(10) Patent No.: US 7,662,155 B2
(45) Date of Patent: Feb. 16, 2010

(54) IMPLANT FOR USE AS REPLACEMENT OF AN ORBITA BOTTOM

(75) Inventors: Marc Christian Metzger, Freiburg (DE); Rainer Schmelzeisen, Freiburg (DE)

(73) Assignee: Synthes USA, LLC, West Chester, PA (US)

( * ) Notice: Subject to any disclaimer, the term of this patent is extended or adjusted under 35 U.S.C. 154(b) by 563 days.

(21) Appl. No.: 11/356,446

(22) Filed: Feb. 16, 2006

(65) Prior Publication Data

US 2007/0156146 A1    Jul. 5, 2007

(30) Foreign Application Priority Data

Dec. 29, 2005   (DE) ............. 10-2005-062-918

(51) Int. Cl.
*A61B 17/80* (2006.01)
*A61F 2/16* (2006.01)
*A61F 2/02* (2006.01)

(52) U.S. Cl. ............. 606/71; 606/70; 606/280; 623/6.43; 623/6.44; 623/17.18; 623/17.19

(58) Field of Classification Search ............... 623/6.64, 623/17.18, 17.19, 23.43, 23.54, 6.44, 6.55; 606/70, 71, 280, 283, 285, 903, 906

See application file for complete search history.

(56) References Cited

U.S. PATENT DOCUMENTS

| 5,139,497 | A | | 8/1992 | Tilghman et al. ............. 606/69 |
|---|---|---|---|---|
| 5,250,048 | A | * | 10/1993 | Gundolf ..................... 606/297 |
| 5,383,931 | A | | 1/1995 | Hehli et al. .................. 623/16 |
| 5,468,242 | A | | 11/1995 | Reisberg ...................... 606/69 |
| 2006/0116682 | A1 | * | 6/2006 | Longo ......................... 606/69 |

FOREIGN PATENT DOCUMENTS

WO   WO 01/72246 A1   10/2001

* cited by examiner

*Primary Examiner*—Thomas J Sweet
*Assistant Examiner*—Yashita Sharma
(74) *Attorney, Agent, or Firm*—Woodcock & Washburn LLP

(57) ABSTRACT

The implant according to the invention is intended to be used as a replacement for an orbita bottom and optionally also for the medial orbita wall. The implant comprises the form of a single-piece preformed plate or grid which comprises a first segment, a second segment and a third segment. The first segment is designed in accordance with the form of the orbita bottom and the second segment is designed according to the form of the medial side-wall. The first and second segments adjoin each other along a first preset breaking line. The third segment adjoins the first segment and is arranged for fixing the implant to the lateral orbita edge.

21 Claims, 6 Drawing Sheets

IMPLANT FOR USE AS REPLACEMENT OF AN ORBITA BOTTOM

BACKGROUND OF THE INVENTION

1. Field of the Invention

The present invention relates to a preformed areal implant for an orbita which can be used as a replacement for an orbita bottom and optionally also for the medial orbita wall.

2. Description of the Related Art

For surgical treatment of fractures in the orbita, inter alia meshes (grids) or plates made of titan or other materials are used. These are available in different patterns and strengths and are designed to be flat for distribution purposes.

Intraoperatively, the surgeon has to fold and bend these meshes manually in order to reproduce the desired anatomical structures. Here, it is not always possible to reach, to clearly define and to reconstruct the deeper anatomical structures of the orbita funnel. Moreover, the result strongly depends on the experience of the surgeon.

If a defect in a deeper part of the orbita cannot be compensated for, the consequences are double images (diplopia), sinking-in of the eye (enopthalmus) and disturbances of motility. In the worst case, excessive manipulation on the eye or on the optical nerve during the operation may result in the loss of sight, so the meshes should not be inserted into the orbita too many times. US 2004/0054372 A1 discloses a fully biodegradable fiber reinforced composite adapted for use as a medical implant and a method for obtaining an anatomically shaped preform.

SUMMARY OF THE INVENTION

The object of the present invention is to provide an anatomically preformed areal implant for use as a replacement for an orbita bottom and optionally also for the medial orbita wall which enables an improved structure reproduction and a simplification for the surgeon.

The object is achieved in accordance with the present invention by means of an implant as defined in claim 1. The implant according to the invention has the major advantage that it is form-closed with the orbita bottom and the medial wall and that it ideally replaces or reconstructs the essential anatomical structures.

An underlying idea of the present invention is that the implant for use as a replacement of an orbita bottom is built in the form of a single-piece preformed plate which comprises a first segment, a second segment and a third segment. The first segment is designed in accordance with the form of the orbita bottom, and the second segment is designed in accordance with the form of the medial side-wall. They adjoin each other along a first preset breaking line. The third segment adjoins the first segment and is arranged for attaching the implant at the lateralo-caudale orbita edge.

The three-segment construction enables a safe insertion of the implant during an operation. The implant is precisely fitted in the eye socket by the second insert segment. During the operation, the implant is displaced in the eye socket into the direction of the medial side-wall, until the second segment or the first preset breaking line adjoins the latter. The depth to which the implant is to be inserted into the eye socket is determined by the third segment.

Frequently, a damage to the orbita bottom goes along with a damage to the medial orbita wall. A reconstruction of the medial orbita wall is ensured by the second segment. If the of the pre-operative check-up reveals that the medial orbita wall is intact, the surgeon can easily remove the segment from the implant along the preset breaking line.

The implant is suited for the reconstruction of the orbita bottom. According to the convex curvature of the eye socket or the eye, the first segment can be curved in a convex form at least in a front section which adjoins the latero-caudale orbita edge. In a more deeply located region of the eye socket there is an elevation, namely a convex curvature directed into the eye socket. During an operation, only the convex part of the orbita bottom in the vicinity of the lateral orbita edge below the eye is essentially visible to the surgeon. Therefore, he has considerable difficulty to manually reconstruct the concave elevation in the implant in a correct anatomical form during the operation. Extensive tests have shown that the elevation is essentially for the alignment and support of the eye in the eye socket. Deviations of the elevation regarding location and height of more than 1 mm already cause significant misalignments of the eye and sight disturbances. According to the invention, is has been recognized that the elevation is essential. With this elevation, the implant is preformed anatomically correctly. An adoption of the form by the surgeon is therefore not necessary.

Thorough examinations of scull forms reveal that the individual deviations of the eye sockets are only minimal and that the eye sockets can essentially be categorized into twelve different categories. Therefore, also only twelve different preformed implants are necessary. The choice of the correct implant can be determined by the surgeon based on simply identifiable characteristics of the patient such as sex, diameter of the eye, etc.

The manufacture of an implant can be achieved in a method as described in the unpublished earlier German application DE 10 2004 058 427. Particularly, DE 10 2004 058 427 also discloses methods for determining the form of the orbita bottom of the medial side-wall and the lateral orbita edge.

Embodiments and preferred refinements are defined in the dependent claims.

The third segment may be preformed in accordance with the lateral orbita edge.

According to an embodiment, the implant comprises a second preset breaking line in the first segment for separating a part of the first segment which is turned away from the third segment from the implant. The depth of the eye socket is a parameter that may individually vary. It may be determined by a simple examination before the operation. An adoption of the length of the implant can be achieved by shortening it along the second preset breaking line.

In another embodiment, the implant comprises a mesh instead of a plate. The first and/or second preset breaking line can run along a grid stay. This enables a smooth edge after breaking away partial pieces. Thus, upon insertion of the implant, no injuries to the smooth parts of the eye are caused.

The present invention is explained in detail in the following description with reference to the attached figures. In the figures.

In the Figures, the same reference signs denote the same or similar elements.

DESCRIPTION OF THE PREFERRED EMBODIMENTS

Figure 1:
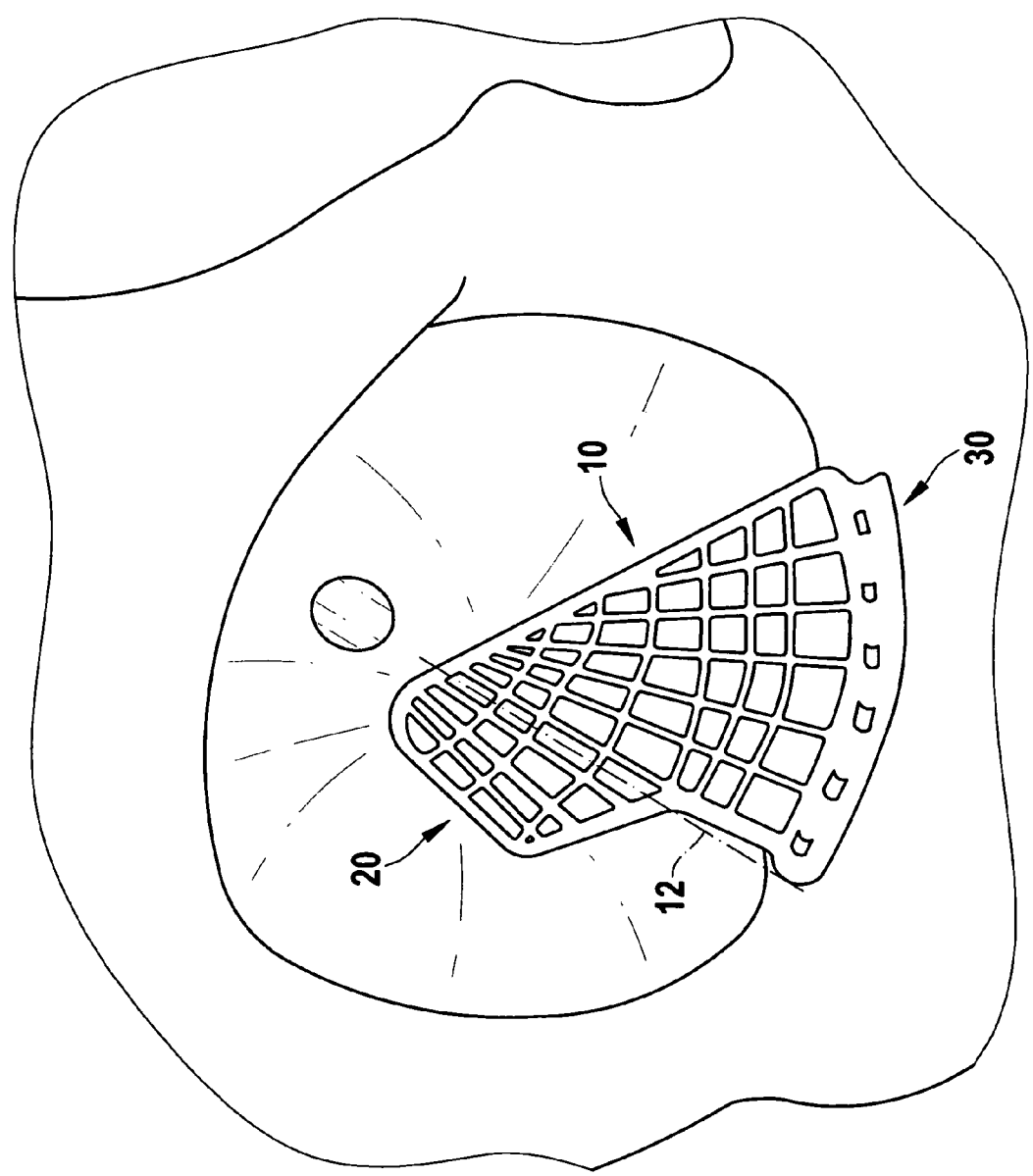
FIG. 1 is an illustration of an eye socket with an inserted implant.

In FIG. 1, the left eye socket of a human being is illustrated. The orbita fraction of the jaw bone, the orbita prolongation of the zygomatic bone and the orbita prolongation of the palatine bone form the orbita bottom. The orbita bottom of the palatine bone forms a small triangular region in the posterior medial corner of the orbita bottom where the orbital bottom adjoins the medial orbita wall. The orbita bottom does not extend horizontally, but elevates with a convex curvature such that the posterior medial part is higher than the areal anterior lateral part. The orbita edge continuously extends along the orbita bottom for approximately 1.0 to 1.5 cm until it adjoins the infraorbital fissure. The central part of the medial orbita wall is thin and steeply declines to the orbita bottom.

In FIG. 1, an embodiment of the implant according to the invention is inserted. A first segment 10 is formed in accordance with the orbita bottom. A second segment 20 is formed in accordance with the medial side-wall. A third segment 30 is formed according to the lateral orbita edge. Along the transition of the medial side-wall in the orbita bottom there is a preset breaking line 12 in the implant. This line runs in the direction of the nervus opticus. The implant can be preferably made as a metallic grid, e.g. from a titan alloy.

Figure 2:
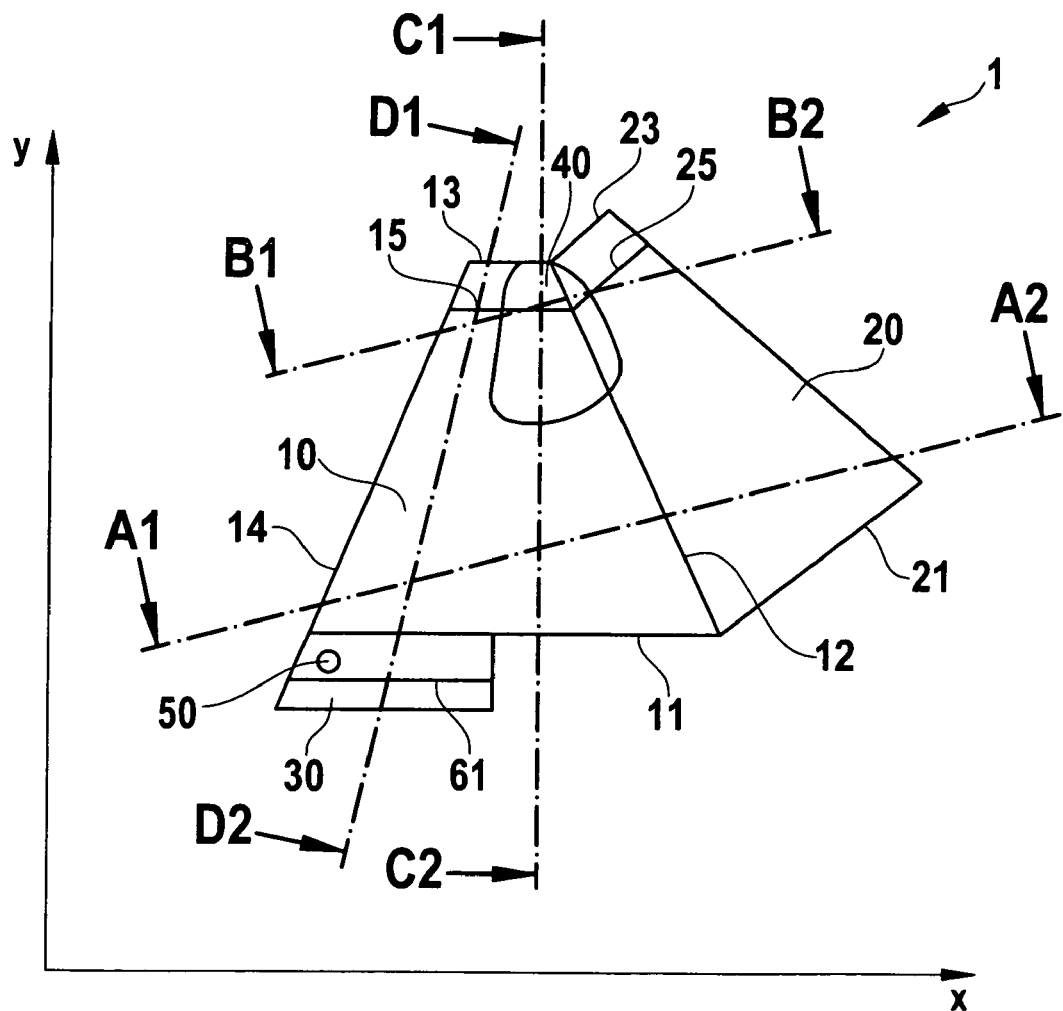
FIG. 2 is a schematical plain view of an embodiment.

In the following embodiments, the geometrical form of the implant is reduced to a few geometrical features. FIG. 2 is a plain view of an embodiment of an implant for replacing the orbita bottom. The form of the implant is segmented into the three segments 10, 20 and 30. The first segment has a trapezoidal form, i.e. a basic side 11 is opposite to a similarly designed side 13. Two sides 12 and 14 form the lateral sides of the trapezoid. The first segment 14 has a slight convex curvature in both the x- and the y-direction. Convex means that the edge comprising the lateral sides and the sides 11 and 13 protrudes from the figure plane farther than the middle of the first segment 10.

Adjoining the side 13 and the lateral sides 12, 14, the first segment 10 includes an elevation 40. In the illustration of FIG. 2, the illustration 40 protrudes from the illustration plane upwards.

The first segment 10 is adapted to the essential structures of the posterior medial part and the anterior lateral part of the eye socket.

A second segment 20 adjoins the first lateral side 12. This is preferably trapezoidal or triangular. The second segment 20 is essentially planar. It is adapted to the form of the medial orbita wall.

A third segment 30 adjoins the basic side 11. Preferably, the third segment 30 does not extend over the full length of the basic side 11, as depicted in FIG. 2. In the third segment 30, one or more bore-holes or vias are provided. These bore-holes are for fixing the implant in the latero-caudale orbita edge by means of a screw or a nail.

Figure 3A:
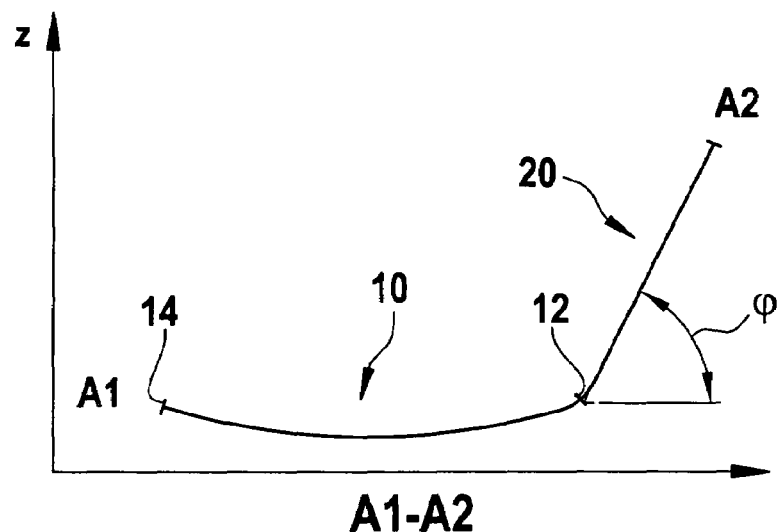
FIG. 3A-3D are cross-sections of the embodiment of FIG. 1 in accordance with the illustrated lines.

In FIG. 3A to 3D, four cross-sections of the implant are illustrated. In FIG. 3A, a cross-section along the line A1-A2 across the first segment 10 and the second segment 20 are illustrated. The first segment 10 comprises a convex curvature in this region as mentioned previously. The second segment 20 is aligned with respect to the first segment in an angle φ of more than 40°. The inclination essentially corresponds to the inclination of the transition of the orbita bottom to the medial orbita wall.

Figure 3B:
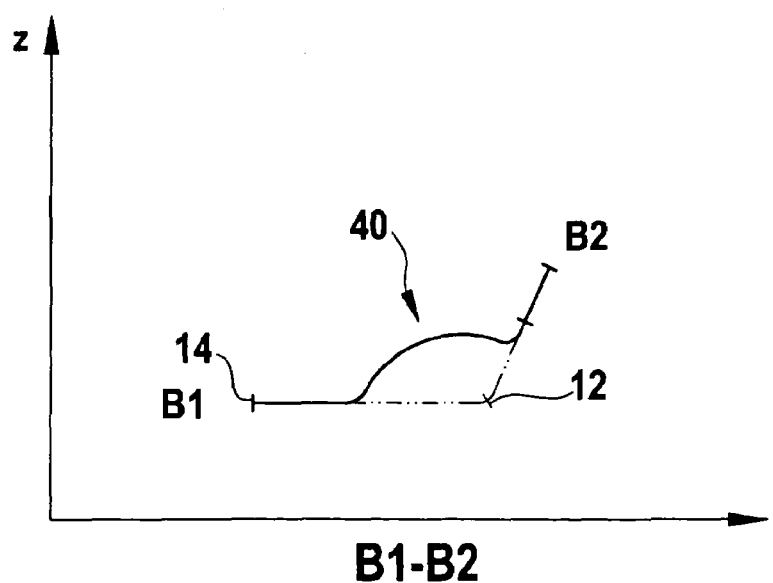
Figure 3C:
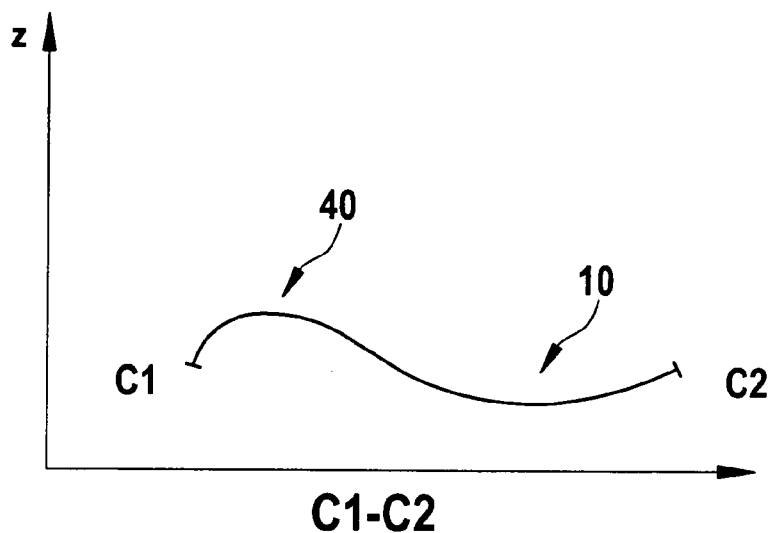
Figure 3D:
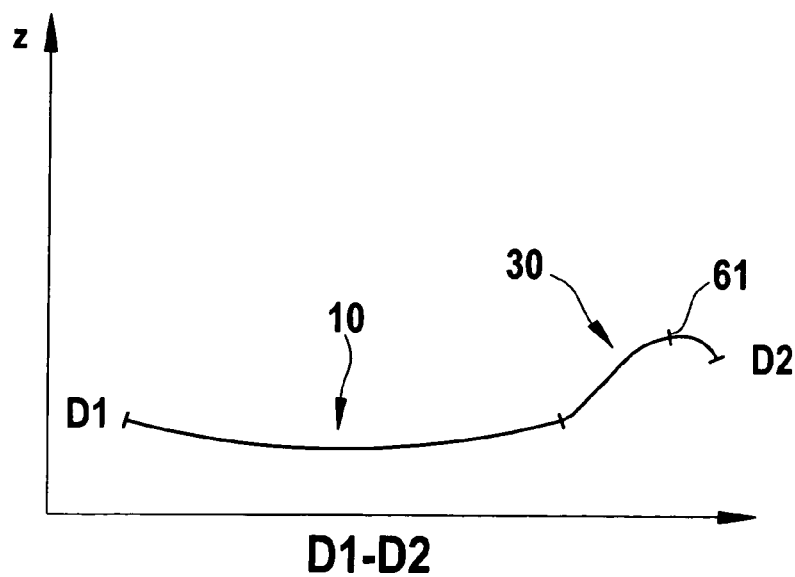

In FIGS. 3B and 3C, two sections along the lines B1-B2 and C1-C2 across the elevation 40 are depicted, respectively. The elevation 40 elevates upwards to the same direction as the second segment 20.

In FIG. 3C, another cross-section in the longitudinal direction of the first segment 10 and the third segment 30 is depicted. The third segment 30 has a curvature with a vertex line 61. The vertex line 61 of the curvature runs approximately in parallel to the basic line 11 of the first segment 10. This curvature is anatomically adapted to the orbita edge. An inserted implant is therefore fixed in the eye socket by means of the form-closed curvature. This facilitates a correct insertion of the implant into the eye socket by a surgeon.

The depth of the implant, i.e. the length of the lateral sides 12, 14 can be adjusted by breaking off a part of the implant 1 along a preset breaking line 15, 25. The depth of the eye socket can be determined individually for any patient by means of a simple measurement.

The second segment 20 mainly serves as a replacement for a damaged medial orbita wall. Should the medial orbita wall be not damaged, the second segment 20 can be broken off by a preformed preset breaking line along the lateral side 12. Occasionally, the surgeon will remove seams along the preset breaking line by means of a sharp blade or rasp.

Figure 4:
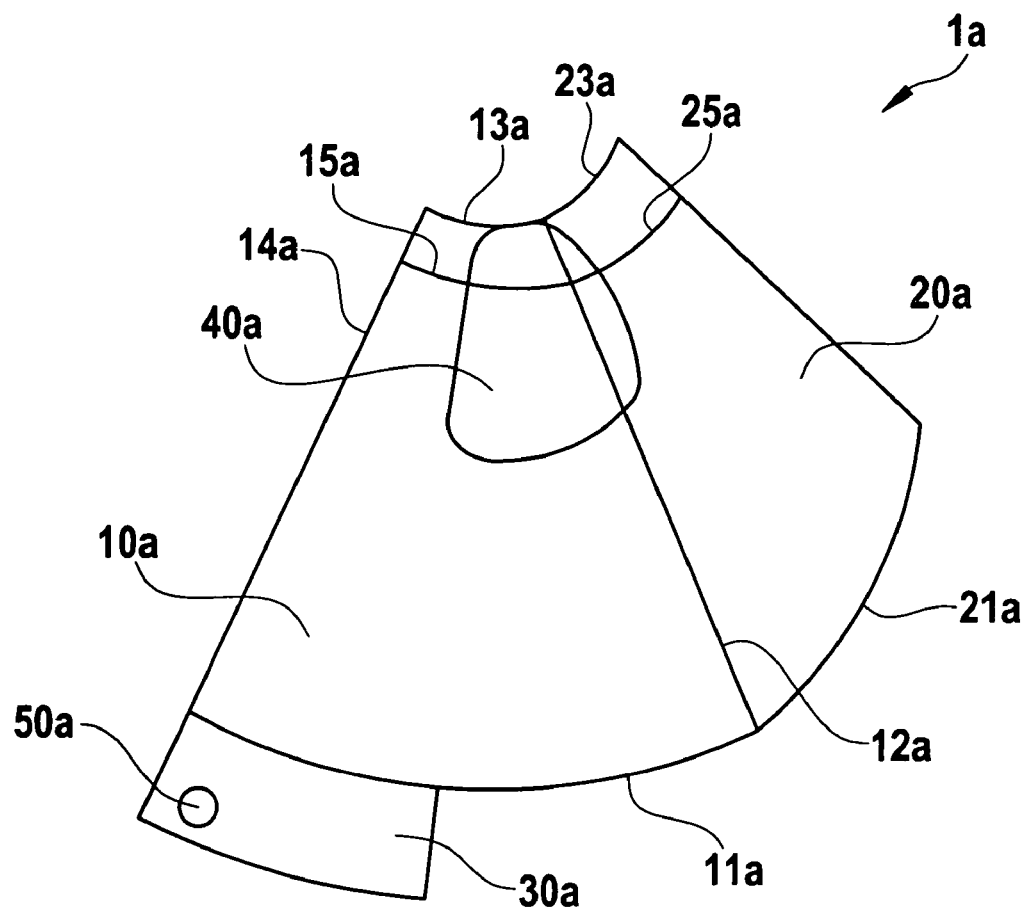
FIG. 4 is a plain view of another embodiment.

In FIG. 4, another embodiment of the implant is shown. In contrast to the preceding embodiments, the basic side 11a and the opposite side 13a are not straight, but curved. A form modified in this way should also be called trapezoidal in accordance with the invention.

The materials used for manufacturing the plate or the grid can be made of titan, titan compounds or tissue-resorbing materials. The thickness of the grid or the plate lies between 0.2 and 1.5 mm.

Figure 5:
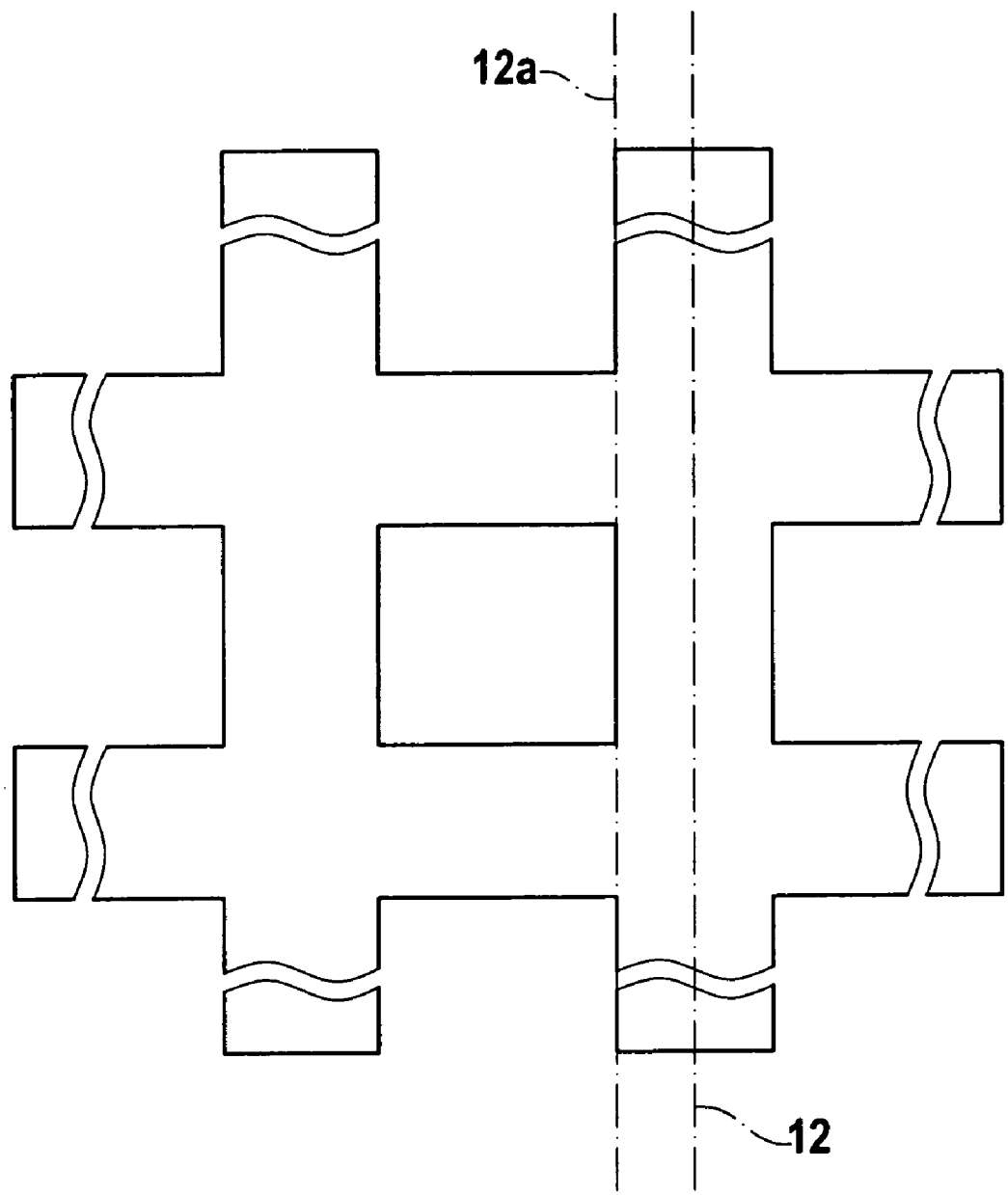
FIG. 5 is a detailed illustration of a preset breaking line of another embodiment.

FIG. 5 shows a detailed view of a preset breaking line 12. Preferably, the preset breaking line runs along or on a grid stay for grid implants. The preset breaking line can also run along line 12a. Upon breaking off, no protruding remainders of grid stays running in cross direction are therefore left. Otherwise, these remainders could cause injuries to the eye upon insertion of the implant.

Although modifications and changes may be suggested by those skilled in the art, it is the intention of the inventor to embody within the patent warranted hereon all changes and modifications as reasonably and properly come within the scope of his contribution to the art.

We claim as our invention:

1. Implant for use as a replacement for an orbita bottom and optionally also for the medial orbita wall in the form of a single-piece preformed plate that comprises a first segment, a second segment and a third segment, and
    wherein the first segment is formed in accordance with an orbita bottom and comprises an elevation, the second segment is formed according to the medial wall, and the second segment is removable from the first segment along a first preset breaking line that adjoins the first and second segments, and
    wherein the third segment is arranged for fixing the implant at a lateral orbita edge.

2. Implant for use as a replacement for an orbita bottom in the form of a single-piece preformed grid that comprises a first segment, a second segment and a third segment, and
    wherein the first segment is formed in accordance with an orbita bottom and comprises an elevation, and the second segment is formed according to the medial side-wall and wherein said first and second segments adjoin along a first preset breaking line, and
    wherein the third segment is arranged for fixing the implant at the lateral orbita edge.

3. Implant according to claim 1, wherein the third segment is formed according to the latero-caudal orbita edge.

4. Implant according to claim 1, wherein said plate comprises a smooth surrounding edge.

5. Implant according to claim 2, wherein said grid comprises a smooth surrounding edge.

6. Implant according to claim 1, wherein a second preset breaking line is provided in said first segment, said second preset breaking line being arranged to remove a part of the first segment which is turned away from the third segment from the implant.

7. Implant according to claim 1, wherein the first preset breaking line runs along a grid stay.

8. Implant according to claim 6, wherein said second preset breaking line runs along a grid stay.

9. Implant according to claim 1, wherein said implant is made of at least one of titan, a titan alloy, plastic, and resorbing materials.

10. Implant according to claim 1, wherein the first segment comprises a convex form proximate to the third segment.

11. Implant according to claim 2, wherein the third segment is formed according to the latero-caudal orbita edge.

12. Implant according to claim 2, wherein a second preset breaking line is provided in said first segment, said second preset breaking line being arranged to remove a part of the first segment which is turned away from the third segment from the implant.

13. Implant according to claim 2, wherein the first preset breaking line runs along a grid stay.

14. Implant to claim 2, wherein said implant is made of at least one of titan, a titan alloy, plastic, and resorbing materials.

15. Implant to claim 6, wherein said implant is made of at least one of titan, a titan alloy, plastic, and resorbing materials.

16. Implant according to claim 2, wherein the first segment comprises a convex form proximate to the third segment.

17. An orbita implant for use to repair an orbita bottom, comprising:
   (a) a first segment, formed in accordance with the orbita bottom, comprising a basic side and an opposite side, a first lateral side extending between the basic side and the opposite side, and an elevation located proximate to the opposite side, wherein the elevation is a convex surface feature on the first segment covering a medically significant portion of the first segment;
   (b) a second segment, formed in accordance to a medial side-wall and angularly offset with respect to the first segment, the second segment removably adjoined to the first segment along a first preset breaking line opposite the first lateral side; and
   (c) a third segment, arranged for fixing the implant at a lateral orbita edge, the third segment connected to the first segment.

18. The orbita implant of claim 17, wherein the first segment further comprises a convex form proximate to the basic side.

19. The orbita implant of claim 17, further comprising a second preset breaking line running at least generally parallel with the basic side of the first segment to adjust the depth of the first segment.

20. The orbita implant of claim 17, wherein the elevation extends into the second segment.

21. The orbita implant of claim 19, wherein the elevation extends distally beyond the second preset breaking line.

* * * * *

UNITED STATES PATENT AND TRADEMARK OFFICE
CERTIFICATE OF CORRECTION

PATENT NO. : 7,662,155 B2
APPLICATION NO. : 11/356446
DATED : February 16, 2010
INVENTOR(S) : Metzger et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 750 days.

Signed and Sealed this

Thirtieth Day of November, 2010

David J. Kappos
*Director of the United States Patent and Trademark Office*